United States Patent [19]
Atef

[11] Patent Number: 5,833,649
[45] Date of Patent: Nov. 10, 1998

[54] METHOD AND KIT FOR DISGUISING TATTOOS

[76] Inventor: Hamid Atef, 4745 W. 160th St., Lawndale, Calif. 90260

[21] Appl. No.: 711,548

[22] Filed: Jan. 6, 1997

[51] Int. Cl.[6] .................................................. A61M 31/00
[52] U.S. Cl. ................................ 604/49; 604/289; 604/1; 606/186
[58] Field of Search ................................ 604/289, 49, 48, 604/51, 110, 114, 22, 1; 607/95; 606/1, 106; 81/9.22

*Primary Examiner*—Mark Bockelman
*Assistant Examiner*—N. Kent Gring

[57] ABSTRACT

A method of concealing tattoos on a person's body includes the steps of adding various coloring pigments to a tattooing ink until a color which matches the person's skin color is achieved. The colored tattoo ink is brushed over the existing tattoo to effect a concealing of the tattoo without the necessity of laser surgery or other radical skin damaging activities. The tattoo ink may also be injected into the tattoo to provide a more permanent concealment. A kit for performing the method of concealment includes a skin color chart for assisting in color selection, and containers having supplies of tattooing ink and coloring pigments. Various swabs, brushes and disposable syringes are also included in the kit.

20 Claims, 3 Drawing Sheets

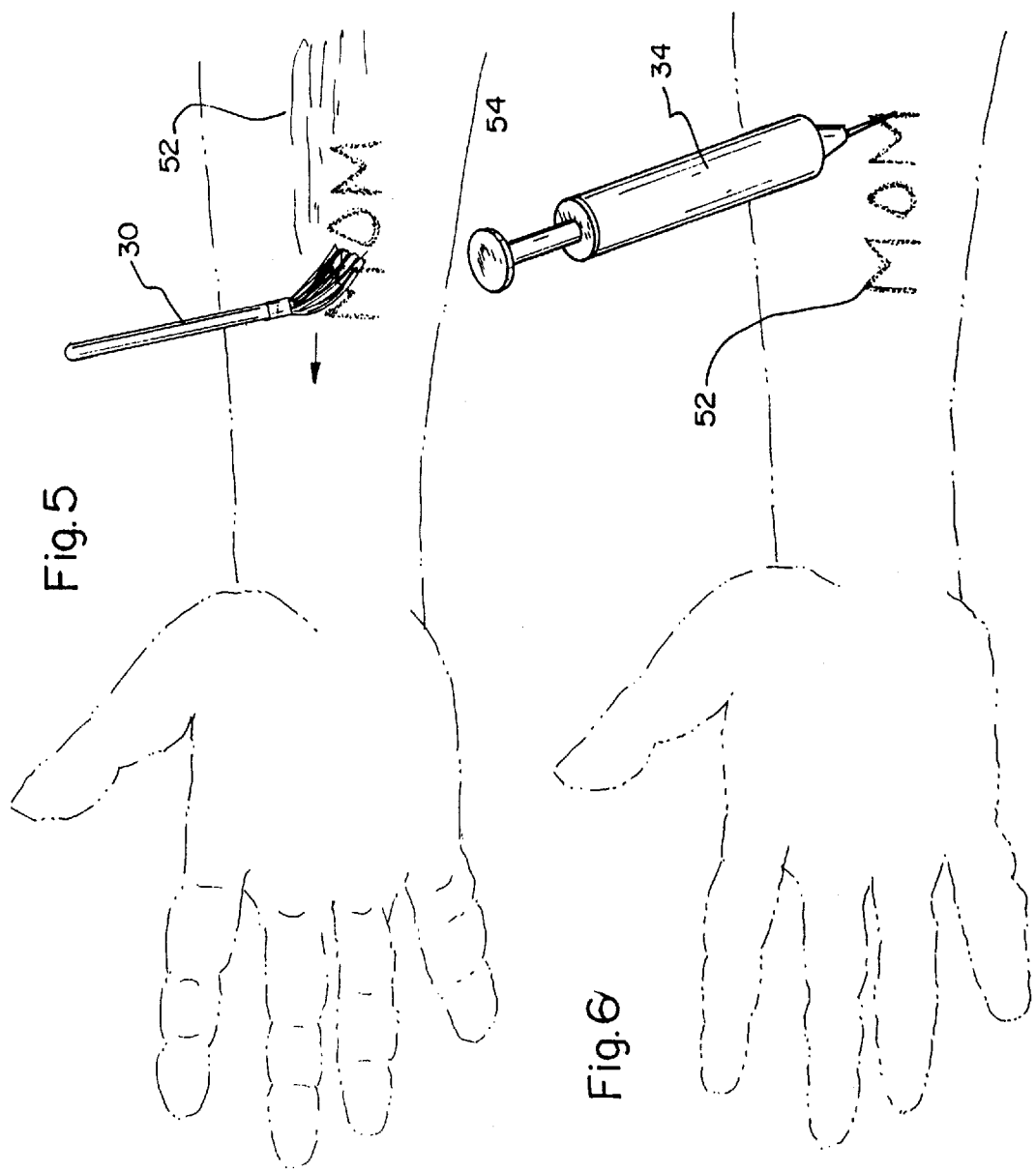

METHOD AND KIT FOR DISGUISING TATTOOS

BACKGROUND OF THE INVENTION

1. Field of the Invention

The present invention relates to tattoos, and more particularly pertains to a method and apparatus for concealing tattoos on a person's body without the necessity of undergoing painful and expensive conventional tattoo removal surgery.

2. Description of the Prior Art

As is well known, many people who obtain tattoos often regret the decision to do so at some later date in time. As such, a substantial commercial market has developed which is directed solely to the removal of unwanted tattoos. To date, the most often utilized method of removing tattoos has involved the use of laser surgery. Unfortunately, laser surgery is quite expensive and often exceeds the cost of initial tattoo acquisition. Needless to say, many people can never hope to afford the expense of laser surgery and accordingly, there exists the need for easier and more reasonable priced methods of removing tattoos. In this respect, the present invention substantially fulfills this need.

SUMMARY OF THE INVENTION

In view of the foregoing disadvantages inherent in the known methods of tattoo removal now present in the prior art, the present invention provides a new method and apparatus for removing tattoos wherein the same can be utilized to effect a reasonable visible concealment of a tattoo without the expense or inconvenience of laser or other skin damaging surgery. As such, the general purpose of the present invention, which will be described subsequently in greater detail, is to provide an apparatus and method for tattoo removal which has many of the advantages of the tattoo removal methods mentioned heretofore and many additional novel features that result in a tattoo removal method and apparatus which is not anticipated, rendered obvious, suggested, or even implied by any of the known prior art, either alone or in any combination thereof.

To attain this, the present invention generally comprises a method of concealing tattoos on a person's body which includes the steps of adding various coloring pigments to a tattooing ink until a color which matches the person's skin color is attained. The colored ink is brushed over the existing tattoo to effect a concealing of the tattoo without the necessity of laser surgery or other radical skin damaging activities. The tattoo ink may also be injected into the tattoo to provide a more permanent concealment. A kit for performing the method of concealment includes a skin color chart for assisting in color selection, and containers having supplies of tattooing ink and coloring pigments. Various swabs, brushes and disposable syringes are also included in the kit.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new tattoo removal method which has many of the advantages of the tattoo removal methods mentioned heretofore and many novel features that result in a tattoo removal method and associated kit which is not anticipated, rendered obvious, suggested, or even implied by any of the known prior art, either alone or in any combination thereof.

It is another object of the present invention to provide a new tattoo removal method and associated kit which may be easily and efficiently manufactured and marketed.

It is a further object of the present invention to provide a new tattoo removal kit and method which is of a durable and reliable design.

An even further object of the present invention is to provide a new tattoo removal kit which is susceptible of a low cost of manufacture with regard to both materials and labor, and which accordingly is then susceptible of low prices of sale to the consuming public, thereby making such tattoo removal kits economically available to the buying public.

Still yet another object of the present invention is to provide a new tattoo removal method and kit which provides in the apparatuses and methods of the prior art some of the advantages thereof, while simultaneously overcoming some of the disadvantages normally associated therewith.

Still another object of the present invention is to provide a new and improved tattoo removal method and kit which facilitates the use of a coloring ink to permanently disguise and conceal an existing tattoo.

Yet another object of the present invention is to provide a new and improved tattoo removal method and kit which facilitates effective tattoo removal without the expense or inconvenience of laser surgery.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is a perspective view illustrating a painting of the colored tattoo ink on a person's skin so as to test for a proper matched color.

FIG. 6 is a perspective view illustrating a permanent impregnation of the colored tattoo ink through a use of a disposable syringe.

DESCRIPTION OF PREFERRED EMBODIMENTS

Figure 1:
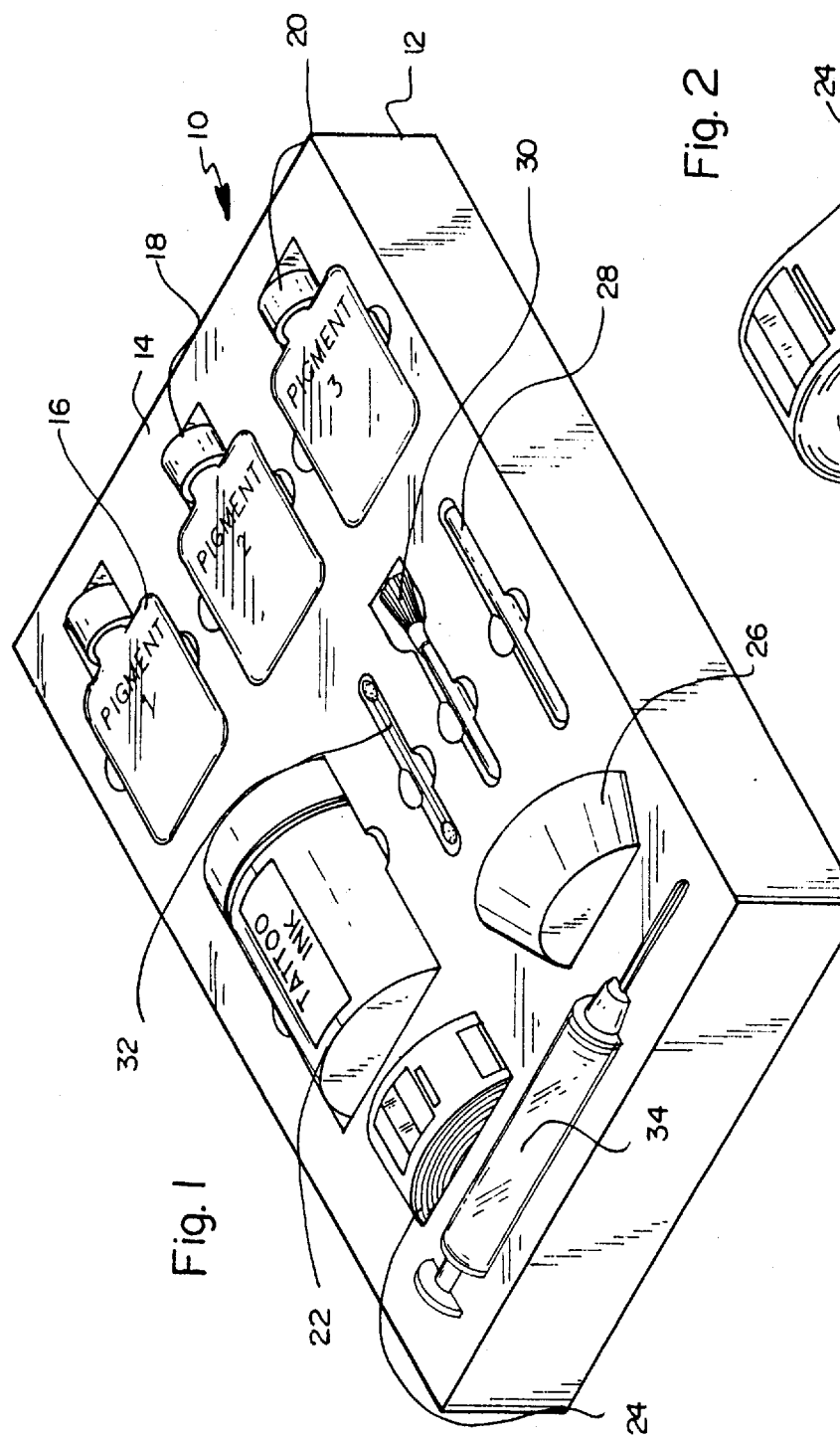
FIG. 1 is a perspective view of a tattoo removal kit forming a part of the present invention.

With reference now to the drawings, and in particular to FIGS. 1–6 thereof, a new tattoo removal method and associated kit embodying the principles and concepts of the present invention and generally designated by the reference numeral 10 will be described.

More specifically and as best illustrated in FIG. 1, it will be noted that the tattoo removal kit 10 effectively consists of a box-like container 12 with a styrofoam or other type of insert 14 conformingly fitted therein. The insert 14 is provided with a plurality of cutouts which are designed to conformingly receive and frictionally retain a plurality of different kit components.

While the kit 10 might contain all types of different components, a preferred embodiment is described and illustrated as having several bottles 16, 18, 20 of different coloring pigments, and these pigments are intended to be mixed with a supply 22 of tattoo ink so as to attain a pre-selected and desired coloring effect in the ink.

The kit 10 further includes a rolled color selection and mixing chart 24 which will be subsequently described in greater detail, and also a small mixing bowl 26 in which the tattoo ink 22 can be selectively mixed with one or more of the coloring pigments 16, 18, 20. A stirring rod 28 is provided to facilitate a mixing of the tattoo ink 22 with the coloring pigments 16, 18, 20, and both a brush 30 and a cotton swab 32 are provided to facilitate the application of the colored ink on a test surface, such as a person's skin. A disposable syringe 34 is also provided in case a person desires to inject the colored ink 22 through a skin surface into a tattoo to effect a more permanent coloring thereof.

Figure 2:
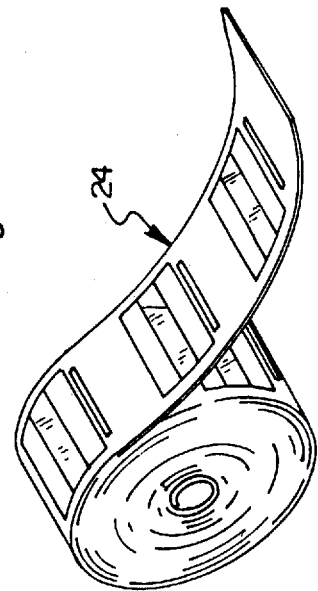
FIG. 2 is a perspective view of a skin color chart roll which forms a part of the present invention.

In performing the method of the present invention, whereby an existing tattoo on a person's skin can be disguised or concealed as opposed to employing laser or some other type of surgery to achieve the same result, it is envisioned that all of the components in the kit 10 might well be employed. Initially, the color chart roll 24, as more clearly shown in FIG. 2, is employed to determine the existing color of the person's skin proximate the tattoo. The color chart 24 is provided as a roll for compact storage and includes a sequential display of a series of gradually changing skin colors.

Figure 3:
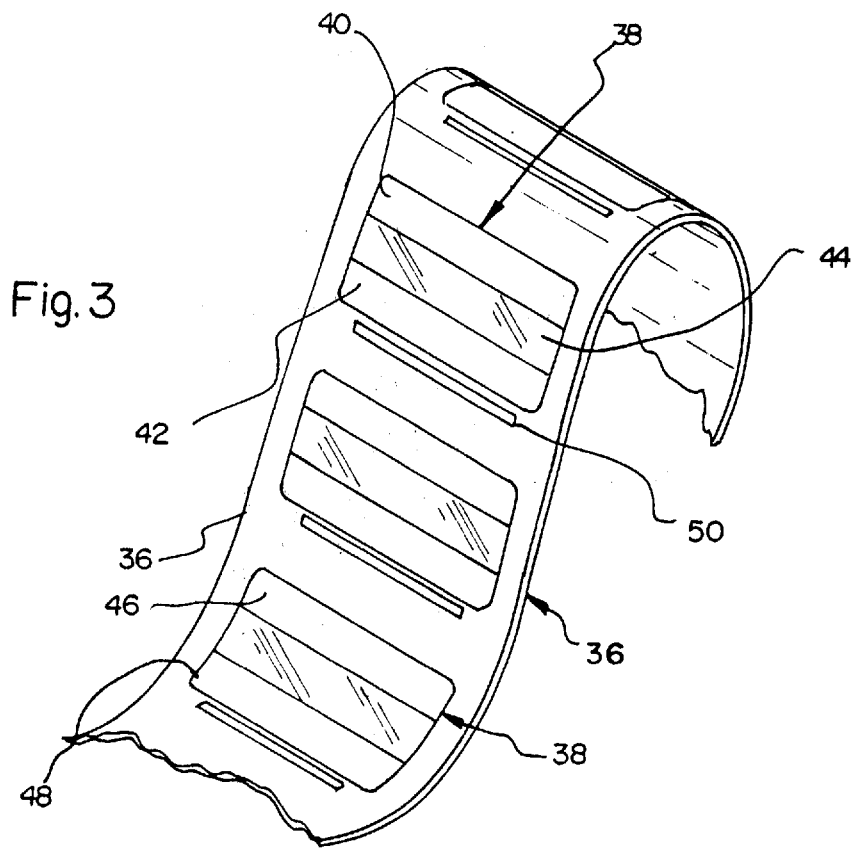
FIG. 3 is an enlarged partial perspective view of the skin color chart roll shown in FIG. 2.

As best illustrated in FIG. 3, a typical strip section 36 of the color chart 24 would typically include a series of rectangular windows, each of which is generally designated by the reference numeral 38. Each window 38 is provided with a differing skin color arrangement and in this regard, a typical window would have two strips 40, 42 in a spaced-apart parallel alignment with a transparent viewing window 44 interconnecting the two and being spaced therebetween. The skin color strips 40,42 would be represent one of many displayed skin colors on the roll chart 24, and they would be identically matched in color.

By this design, it can be seen that the color chart section 36 can be flexibly positioned to overlay a person's skin proximate an existing tattoo, and the strip can be continually slid along the person's skin until the proper color window 38 appears. More specifically, when the proper individual color window 38 is positioned over the person's skin, the color strips 40, 42 will be substantially matched in color to the person's skin color as viewed through the transparent viewing window 44. If the skin color match is not substantially identical, the strip 36 can again be advanced off of the roll 24 whereby another matching set of colors 46, 48 can be caused to overlay the person's skin, and this process is continued until a proper color match is achieved. Once the desired color match is found, a user of the color chart roll 24 need only to look beneath the chosen color window 38 to view a small set of ingredient mixing instructions 50 permanently inscribed beneath each window.

Figure 4:
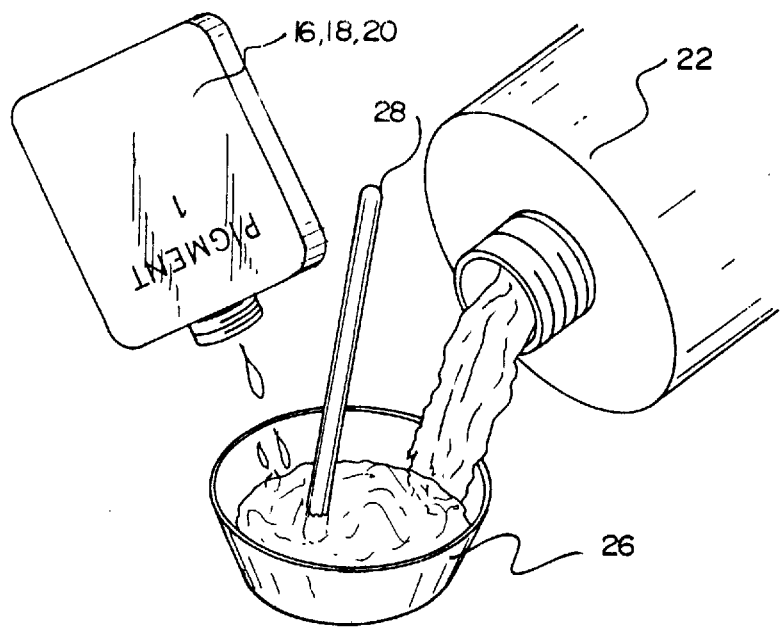
FIG. 4 is a perspective view illustrating the addition of a coloring pigment to a liquid tattoo ink.

As shown in FIG. 4, after the proper color is chosen and the appropriate mixing instructions 50 are found, the small mixing bowl 26 may be used to effect the desired mixing of pigments 16, 18, 20 with the supply tattoo ink 22 in those proportions defined by the mixing instructions. As is apparent, the provided stirring rod 28 can be utilized to stir the mixed ingredients so as to achieve a uniform mix and desired coloring effect.

With reference to FIG. 5, it can be seen that once the desired admixture is obtained, either the brush 30 or the cotton swab 32 can be utilized to spread a test layer of the colored ink 22 over an existing tattoo 52 on a person's skin 54. If the proper adhesives and gums are already present in the ink 22, it may be possible to effectively stain and thus conceal the tattoo 52 simply with a skin surface application. If the colored ink 22 is of an iron-gallotannate solution and is of the proper color, the tattoo 52 will usually permanently disappear. By the same token, if the mixture 22 needs further coloring, more of the coloring pigments 16, 18, 20 can be employed to achieve this result.

As shown in FIG. 6, a more permanent impregnation of the colored ink 22 over a tattoo 52 can be achieved through the use of the provided disposable syringe 34. A supply of the colored ink 22 can be provided in the syringe 34 and injected directly into the tattoo 52 so as to effect a color change which then disguises or conceals the tattoo in a permanent manner.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A method of concealing tattoos so as to effect a visual removal thereof from a person's skin, said method comprising the steps of:
   selecting a first color which effectively matches an existing color of said person's skin proximate said tattoo;
   selecting a medium to be impregnated in said person's skin over said tattoo;
   adding at least one coloring pigment to said medium until said medium is colored to substantially match said first color; and
   applying said medium over said tattoo to determine if said medium effectively covers said tattoo so as to cause said tattoo to match said first color, thereby effecting said concealing of said tattoo.

2. The method of concealing tattoos so as to effect a visual removal thereof from a person's body as described in claim 1 wherein said medium is a liquefied adhesive medium.

3. The method of concealing tattoos so as to effect a visual removal thereof from a person's body as described in claim 2 wherein said medium is a tattooing ink.

4. The method of concealing tattoos so as to effect a visual removal thereof from a person's body as described in claim 1, and further wherein said applying of said medium over said tattoo is accomplished by brushing, thereby to determine a proper coloring effect of said medium relative to said person's skin.

5. The method of concealing tattoos so as to effect a visual removal thereof from a person's body as described in claim 4 wherein said applying of said medium over said tattoo further includes the step of injecting said medium into said person's skin over said tattoo, thereby to cause said tattoo to be changed in color so as to match said existing color of said person's skin.

6. The method of concealing tattoos so as to effect a visual removal thereof from a person's body as described in claim 5 wherein said medium is a liquefied adhesive medium.

7. The method of concealing tattoos so as to effect a visual removal thereof from a person's body as described in claim 6 wherein said medium is a tattooing ink.

8. The method of concealing tattoos so as to effect a visual removal thereof from a person's body as described in claim 1 wherein said medium includes an iron-gallotannate ink.

9. A kit utilizable to effect a concealing of tattoos on a person's skin, said kit including:
   a color chart for determining a first color which effectively matches a color of said person's skin proximate said tattoo;
   a first supply of a medium to be applied to said person's skin;
   a second supply of at least one coloring pigment to be mixed with said medium to effect a selective coloring of said medium until said medium effectively matches said first color, thereby to create a colored medium which can be used to conceal said tattoo; and
   a first applicator for applying said colored medium to said person's skin over said tattoo.

10. The kit utilizable to effect a concealing of tattoos on a person's skin as described in claim 9, said kit further including a second applicator for applying said colored medium to said person's skin over said tattoo.

11. The kit utilizable to effect a concealing of tattoos on a person's skin as described in claim 10, wherein said second applicator is a syringe.

12. The kit utilizable to effect a concealing of tattoos on a person's skin as described in claim 10, wherein said first applicator is a brush.

13. The kit utilizable to effect a concealing of tattoos on a person's skin as described in claim 10, wherein said first applicator is a swab.

14. The kit utilizable to effect a concealing of tattoos on a person's skin as described in claim 9, wherein said first applicator is a brush.

15. The kit utilizable to effect a concealing of tattoos on a person's skin as described in claim 9, wherein said first applicator is a swab.

16. The kit utilizable to effect a concealing of tattoos on a person's skin as described in claim 9, wherein said medium is a liquefied adhesive medium.

17. The kit utilizable to effect a concealing of tattoos on a person's skin as described in claim 16, wherein said medium is a tattooing ink.

18. The kit utilizable to effect a concealing of tattoos on a person's skin as described in claim 17, wherein said tattooing ink includes iron-gallotannate ink.

19. The kit utilizable to effect a concealing of tattoos on a person's skin as described in claim 9, wherein said color chart includes at least one set of parallelly aligned, spaced apart color sections, each of said color sections of being of an identical color to the other and being interconnected by a transparent viewing window positioned therebetween, whereby when said color chart is positioned over a person's skin, said person's skin color will be viewable through said transparent viewing window so as to be visibly comparable to said set of color sections positioned on opposed sides of said transparent viewing window.

20. A method of concealing tattoos so as to effect a visual removal thereof from a person's skin, said method comprising the steps of:
   holding a color chart against said person's skin to effect a choosing of a first color which substantially matches said person's skin;
   reading a set of directions on said color chart for mixing at least one coloring pigment with a selected medium to be impregnated in said person's skin over said tattoo;
   adding said at least one coloring pigment to said medium until said medium is colored to substantially match said first color on said color chart;
   confirming a proper medium color by holding said color chart proximate said medium;
   applying an initial coating of said medium over said tattoo to determine if said medium effectively covers said tattoo so as to cause said tattoo to match said first color, thereby effecting a concealing of said tattoo;
   removing said initial coating of said medium over said tattoo; and
   applying a second coating of said medium over said tattoo by injecting said medium into said person's skin over said tattoo, thereby to cause said tattoo to be permanently changed in color so as to match said existing color of said person's skin.

* * * * *